(12) United States Patent
Shah

(10) Patent No.: US 7,875,242 B2
(45) Date of Patent: Jan. 25, 2011

(54) SLIDE STAINER WITH MULTIPLE HEATER STATIONS

(76) Inventor: Preyas Sarabhai Shah, 591 10th Ave., Warminister, PA (US) 18974

( * ) Notice: Subject to any disclaimer, the term of this patent is extended or adjusted under 35 U.S.C. 154(b) by 798 days.

(21) Appl. No.: 11/581,834

(22) Filed: Oct. 17, 2006

(65) Prior Publication Data

US 2008/0089808 A1    Apr. 17, 2008

(51) Int. Cl.
*G01N 21/00*    (2006.01)
(52) U.S. Cl. .............................. 422/65; 422/63; 422/64; 422/67; 422/99; 422/100; 436/46; 436/174; 436/180
(58) Field of Classification Search .............. 422/63–67, 422/99–100; 436/180, 46, 174
See application file for complete search history.

(56) References Cited

U.S. PATENT DOCUMENTS

| | | | |
|---|---|---|---|
| 4,738,824 A | 4/1988 | Takeuchi | |
| 5,180,606 A | 1/1993 | Stokes et al. | |
| 5,336,467 A | 8/1994 | Heidt et al. | |
| 5,601,650 A * | 2/1997 | Goldbecker et al. | 118/697 |
| 6,017,495 A | 1/2000 | Ljungmann | |
| 6,080,363 A | 6/2000 | Takahashi et al. | |
| 6,093,574 A | 7/2000 | Druyor-Sanchez et al. | |
| 6,268,208 B1 | 7/2001 | Kondo | |
| 6,319,470 B1 | 11/2001 | Lefevre et al. | |
| 6,358,473 B1 | 3/2002 | Coello et al. | |
| 6,387,326 B1 | 5/2002 | Edwards et al. | |
| 6,436,348 B1 | 8/2002 | Ljungmann et al. | |
| 6,444,170 B1 | 9/2002 | Heid et al. | |
| 6,495,106 B1 | 12/2002 | Kalra et al. | |
| 6,541,261 B1 | 4/2003 | Bogen et al. | |
| 6,558,623 B1 | 5/2003 | Ganz et al. | |
| 6,572,824 B1 | 6/2003 | Ostgaard et al. | |
| 6,594,537 B1 | 7/2003 | Bernstein et al. | |
| 6,735,531 B2 | 5/2004 | Rhett et al. | |
| 6,746,851 B1 | 6/2004 | Tseung et al. | |
| 6,752,960 B1 | 6/2004 | Matsubara et al. | |
| 6,756,015 B2 | 6/2004 | Dalkidis et al. | |
| 6,783,733 B2 | 8/2004 | Bogen et al. | |
| 6,800,249 B2 | 10/2004 | de la Torre-Bueno | |
| 6,803,018 B1 | 10/2004 | Stiller | |
| 6,821,072 B2 | 11/2004 | Thiem et al. | |
| 6,827,900 B2 | 12/2004 | Thiem et al. | |
| 6,827,901 B2 | 12/2004 | Copeland et al. | |
| 6,855,292 B2 | 2/2005 | Angros | |
| 6,855,552 B2 | 2/2005 | Towne et al. | |

(Continued)

FOREIGN PATENT DOCUMENTS

WO    WO 2004/055497 A1    7/2004

*Primary Examiner*—Jyoti Nagpaul
(74) *Attorney, Agent, or Firm*—Ratner Prestia

(57) ABSTRACT

Apparatus and methods for treating hematological, cytological, or histological specimens deposited on slides are disclosed. The apparatus comprises a first heating station, a second heating station, and at least one processing station adapted to receive specimen slides. A lifting device moves a first set of the specimen slides and a second set of the specimen slides among the first heating station, the second heating station, and the at least one processing station. A controller independently controls the temperature of the first and second heating stations and selectively positions each of the first and second sets of specimen slides within at least two of the first heating station, the second heating station, and the at least one processing station.

18 Claims, 7 Drawing Sheets

U.S. PATENT DOCUMENTS

| | | |
|---|---|---|
| 2002/0018733 A1 | 2/2002 | Kapplein et al. |
| 2002/0031445 A1 | 3/2002 | Thiem et al. |
| 2002/0051735 A1 | 5/2002 | Dorenkamp et al. |
| 2002/0054829 A1 | 5/2002 | Dalkidis et al. |
| 2002/0057992 A1 | 5/2002 | Eckert et al. |
| 2002/0064482 A1* | 5/2002 | Tisone et al. ............... 422/100 |
| 2002/0076351 A1 | 6/2002 | Wernz et al. |
| 2002/0090730 A1 | 7/2002 | Eckert et al. |
| 2002/0090731 A1 | 7/2002 | Gropp et al. |
| 2002/0098118 A1 | 7/2002 | Eckert et al. |
| 2002/0110494 A1 | 8/2002 | Lemme et al. |
| 2002/0111743 A1 | 8/2002 | Gropp |
| 2003/0099573 A1 | 5/2003 | Tseung et al. |
| 2004/0002163 A1 | 1/2004 | Reinhardt et al. |
| 2004/0005244 A1 | 1/2004 | Thiem |
| 2004/0033163 A1 | 2/2004 | Tseung et al. |
| 2004/0043495 A1 | 3/2004 | Stokes et al. |
| 2004/0052685 A1 | 3/2004 | Richards et al. |
| 2004/0241050 A1 | 12/2004 | Bogen et al. |
| 2004/0266015 A1 | 12/2004 | Favuzzi et al. |

* cited by examiner

SLIDE STAINER WITH MULTIPLE HEATER STATIONS

FIELD OF THE INVENTION

The present invention relates to a slide stainer for treating hematological, histological, or cytological specimens.

BACKGROUND OF THE INVENTION

Currently, many medical tests are performed by examining a biological specimen, e.g., blood, pus, or urine, applied to a slide, such as a conventional glass microscope slide. Typically, the biological specimen is deposited onto the slide and, then, treated with a reagent, such as a stain, to make features of the deposited biological specimen more visible. Often, the slide is then rinsed to remove excess reagent and dried for handling by laboratory personnel.

Automated slide stainers are available which automate the process of staining, rinsing, and drying specimen slides. One type of automated slide stainer is a dip and dunk slide stainer. In a dip and dunk slide stainer, one or more reagents are applied to slides by dipping the slides into one or more vessels containing these reagent. The slides are then rinsed by dipping the slides into a rinsing vessel, supplying water (or rinse solution) to the rinsing vessel, such that the water passes over the slides, and removing the slides from the rinsing vessel. Finally, the slides are dried by circulating air over them.

Present dip and dunk stainers, however, require one process to finish before another process may be started. Some slides may require different durations of time in different vessels, depending on the slides and the reagent in the vessels. Such situations may cause backups in the staining process, resulting in delays and reducing the efficiency of the staining process. The present invention addresses this situation, among others.

SUMMARY OF THE INVENTION

Briefly, the invention is embodied in methods and apparatus for treating hematological, cytological, or histological specimens deposited on slides. An exemplary apparatus comprises a first heating station, a second heating station, and at least one processing station adapted to receive one or more specimen slides. A lifting device is configured to move a first set of specimen slides and a second set of specimen slides among a plurality of the first heating station, the second heating station, and the at least one processing station. A controller is operatively coupled to the first and second heating stations to independently control the temperature of the first and second heating stations and operatively coupled to the lifting device to selectively position each of the first and second sets of specimen slides within at least two of the plurality of the first heating station, the second heating station, and the at least one processing station.

An exemplary method comprises placing a first set of specimen slides into a first heating station; placing a second set of specimen slides into a second heating station; removing each of the first and second sets of specimen slides from its respective heating station; and placing each of the first and second sets of specimen slides in a plurality of processing stations in a predetermined non-sequential order.

Another exemplary method comprises placing a first set of specimen slides into a first heating station; heating the first set of specimen slides with the first heating station to remove a coating from the first set of specimen slides; placing a second set of specimen slides into a second heating station; heating the second set of specimen slides with the second heating station to remove a coating from the second set of specimen slides; removing the first set of specimen slides from the first heating station and placing the first set of specimen slides into a first slide processing station; and removing the second set of specimen slides from the second heating station and placing the second set of specimen slides into a second slide processing station.

BRIEF DESCRIPTION OF THE DRAWINGS

The foregoing summary, as well as the following detailed description of desired embodiments of the invention, will be better understood when read in conjunction with the appended drawings, which are incorporated herein and constitute part of this specification. For the purposes of illustrating the invention, there are shown in the drawings exemplary embodiments of the invention. It should be understood, however, that the invention is not limited to the precise arrangements and instrumentalities shown. In the drawings, the same reference numerals are employed for designating the same elements throughout the several figures. In the drawings.

DETAILED DESCRIPTION OF THE INVENTION

Figure 1:
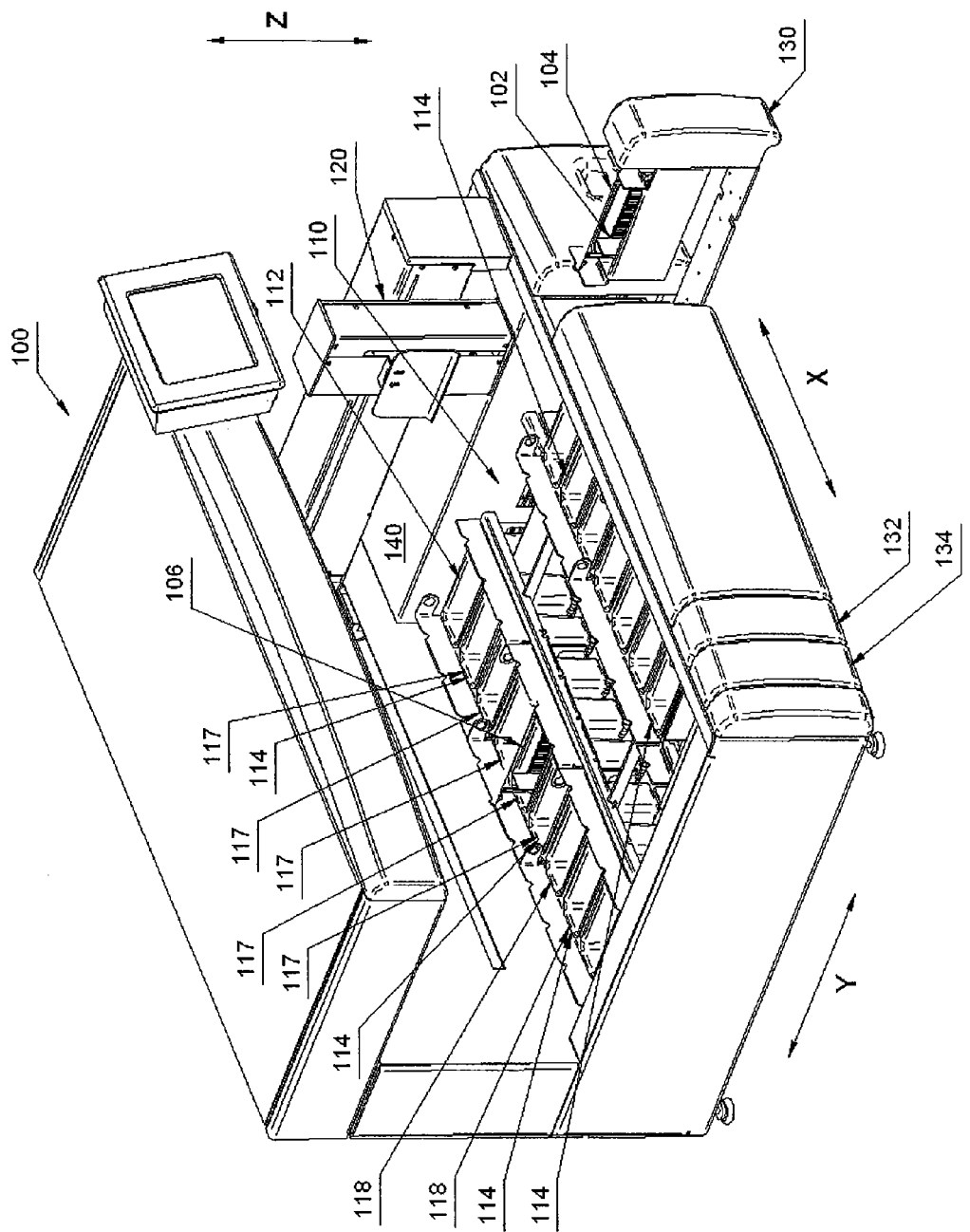
FIG. 1 is a perspective view of a slide stainer according to an exemplary embodiment of the present invention, with a set of slides being loaded into a loading station.

Certain terminology is used herein for convenience only and is not to be taken as a limitation on the present invention. The terminology includes the words specifically mentioned, derivatives thereof and words of similar import. The following describes exemplary embodiments of the invention. It should be understood based on this disclosure, however, that the invention is not limited by the exemplary embodiments of the invention.

Referring now to the Figures in general, an apparatus 100 for treating hematological, cytological, or histological specimen slides 102 is disclosed. A specimen slide 102 is a slide having a biological specimen disposed thereon. Apparatus 100 may be used to remove a coating from specimen slides 102, stain specimen slides 102, rinse specimen slides 102, and/or perform other operations known to be performed in such devices.

Referring specifically to FIGS. 1-5, apparatus 100 includes a first heating station 110, a second heating station 112, and a plurality of processing stations 114. Each station 110, 112, 114 is adapted to receive one or more specimen slides 102. A lifting device 120 is configured to move a first set 104 of the one or more specimen slides 102 and a second set 106 of the one or more specimen slides 102 among a plurality of first heating station 110, second heating station 112, and processing stations 114. As used herein, the term "set" is defined to mean "one or more." Processing stations 114 may include other heating stations (such as heating stations 110, 112), rinse stations 117, staining stations 118, and other such stations for processing specimen slides.

Apparatus 100 also includes a loading drawer 130 that is used to load specimen slides 102 into apparatus 100. Also, two removal drawers 132, 134 are provided for removing specimen slides 102 from apparatus 100 after all processing has been performed on specimen slides 102 in apparatus 100. While two removal drawers 132, 134 are shown in the exemplary embodiment, those skilled in the art will recognize that more or less than two removal drawers 132, 134 may be used. The plurality of removal drawers 132, 134 allows specimen slides 102 to be removed from apparatus 100 while reducing the likelihood of having to stop any processing being performed in any of the other processing stations 114.

Including heating stations 110, 112, loading drawer 130 and removal drawers 132, 134, apparatus 100 includes thirty processing stations 114 arranged in a matrix having three rows with ten processing stations 114 per row. Those skilled in the art will recognize that apparatus 100 may include more or less than thirty processing stations 114 that are arranged in a matrix of at least two rows.

Apparatus 100 also includes a controller 140 operatively coupled to first and second heating stations 110, 112, respectively, to independently control the temperature of first and second heating stations 110, 112. Controller 140 is also operatively coupled to lifting device 120 to selectively position each of the first and second sets 104, 106 of specimen slides within at least two of the plurality of first heating station 110, second heating station 112, and processing stations 114. Controller 140 is enclosed within a housing of apparatus 100 to protect controller 140 from the external environment. Suitable controllers for use with apparatus 100 will be understood by one of skill in the art from the description herein.

Lifting device 120 is operatively coupled to controller 140 to move specimen slides 102 in three orthogonal directions: longitudinally along the X axis, laterally along the Y axis, and vertically along the Z axis, shown in FIGS. 1-5. Lifting device 120 may move specimen slides 102 in one of the three orthogonal directions as directed by controller 140 at any one time or, alternatively, lifting device 120 may combine at least two of the three orthogonal directions in a single movement.

Lifting device 120 is configured to position each of first and second sets 104, 106 of specimen slides 102 as directed by controller 140. Controller 140 is operatively coupled with lifting device 120 to selectively position first and second sets 104, 106 of specimen slides 102 into at least one of the plurality of processing stations 114 and into at least one of the plurality of removal drawers 132, 134 in a predetermined sequential or non-sequential order.

Figure 2:
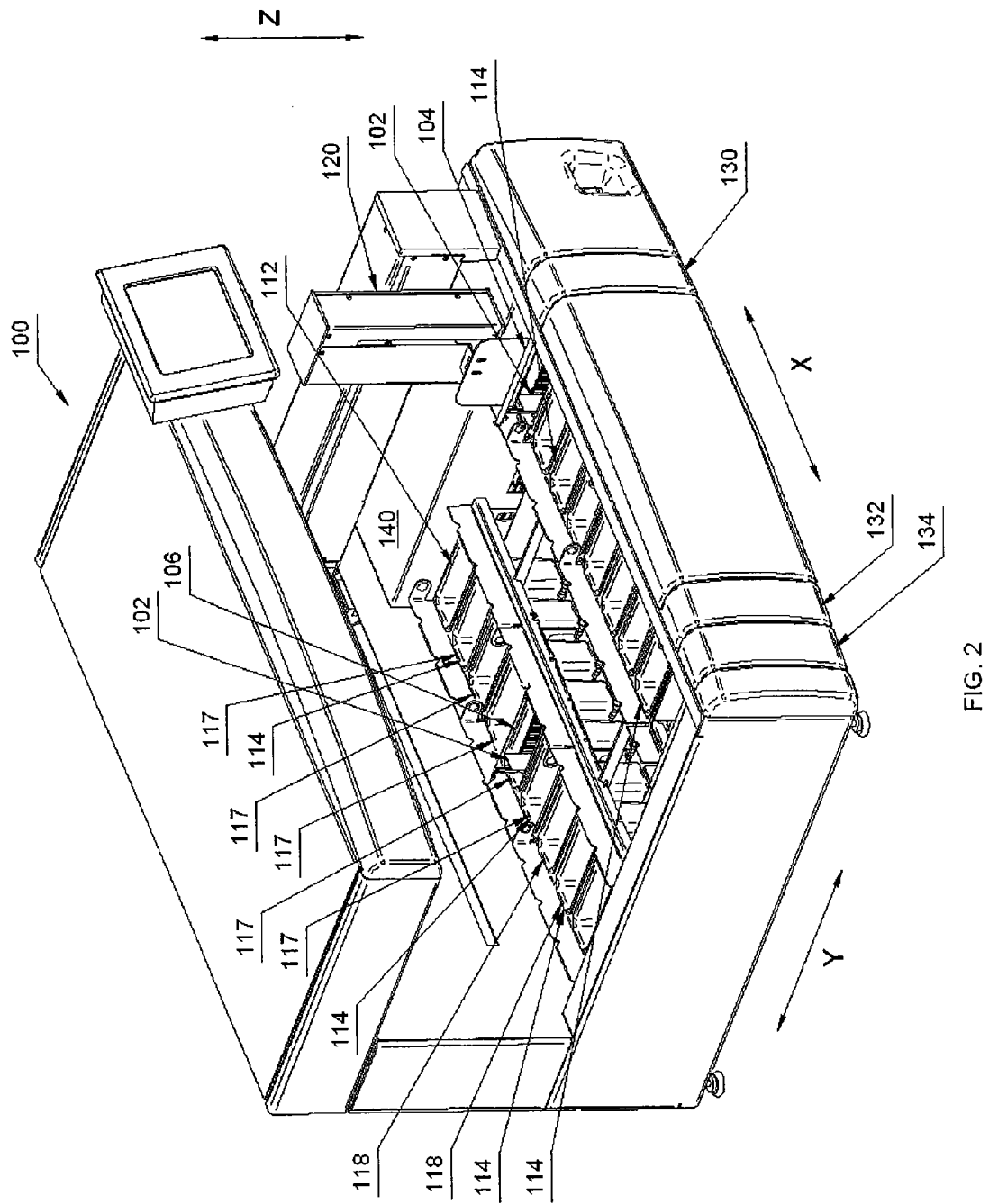
FIG. 2 is a perspective view of the slide stainer of FIG. 1, with a lifting device lowered to receive a set of slides from the loading drawer.
Figure 3:
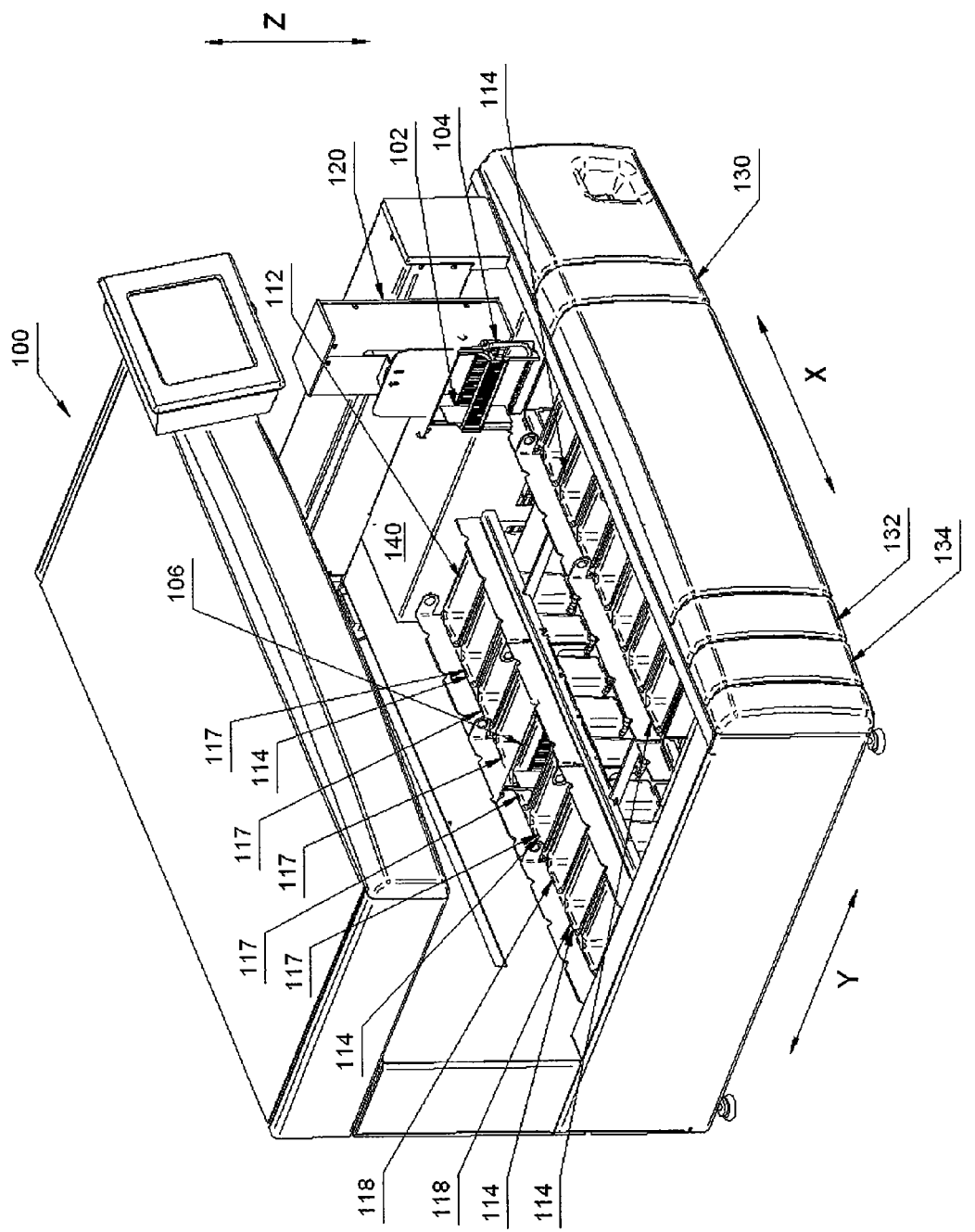
FIG. 3 is a perspective view of the slide stainer of FIG. 1, with the lifting device lifting the set of slides from the loading drawer to a heater station.
Figure 4:
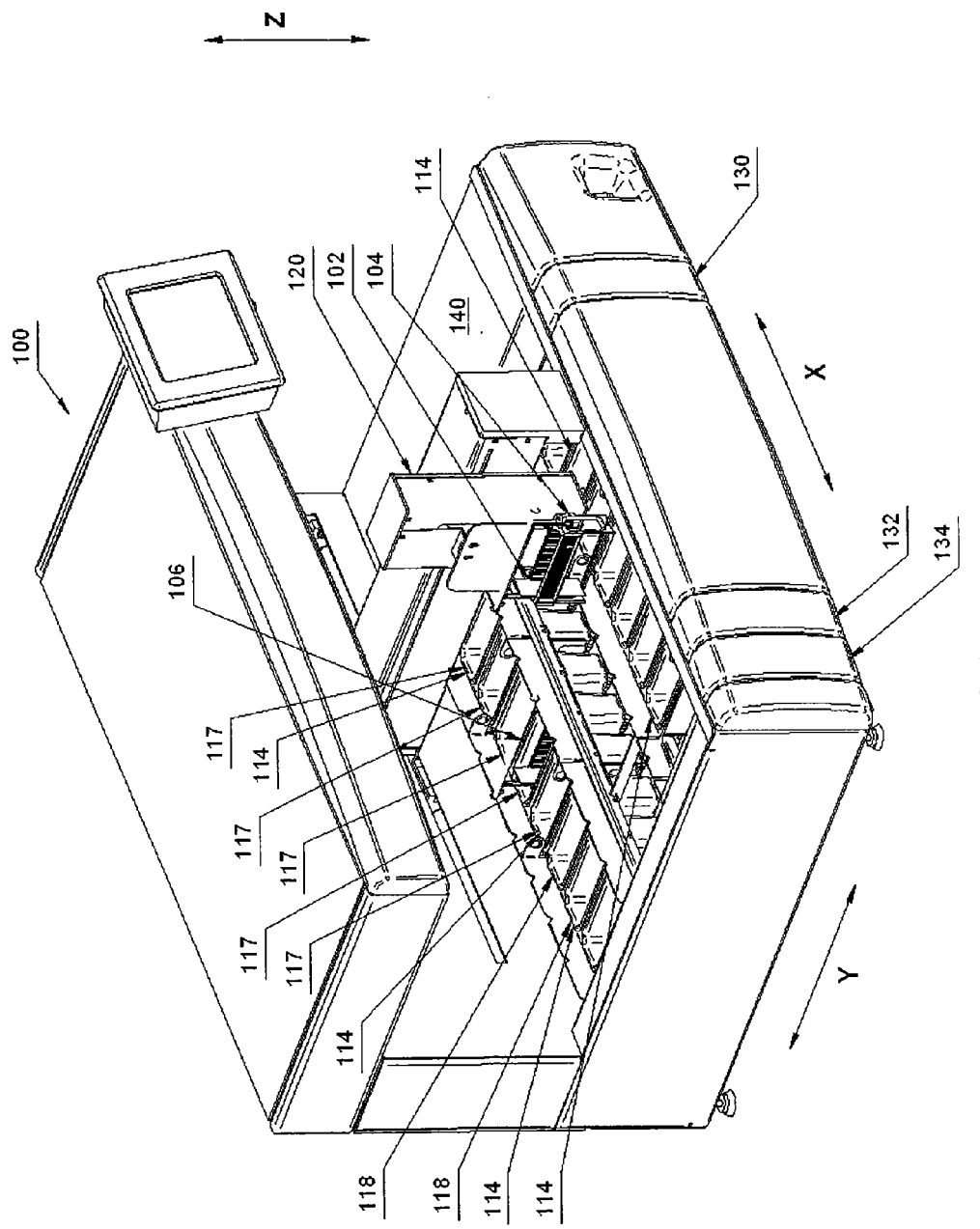
FIG. 4 is a perspective view of the slide stainer of FIG. 1, with the lifting device lifting the set of slides from one processing station to another processing station.
Figure 5:
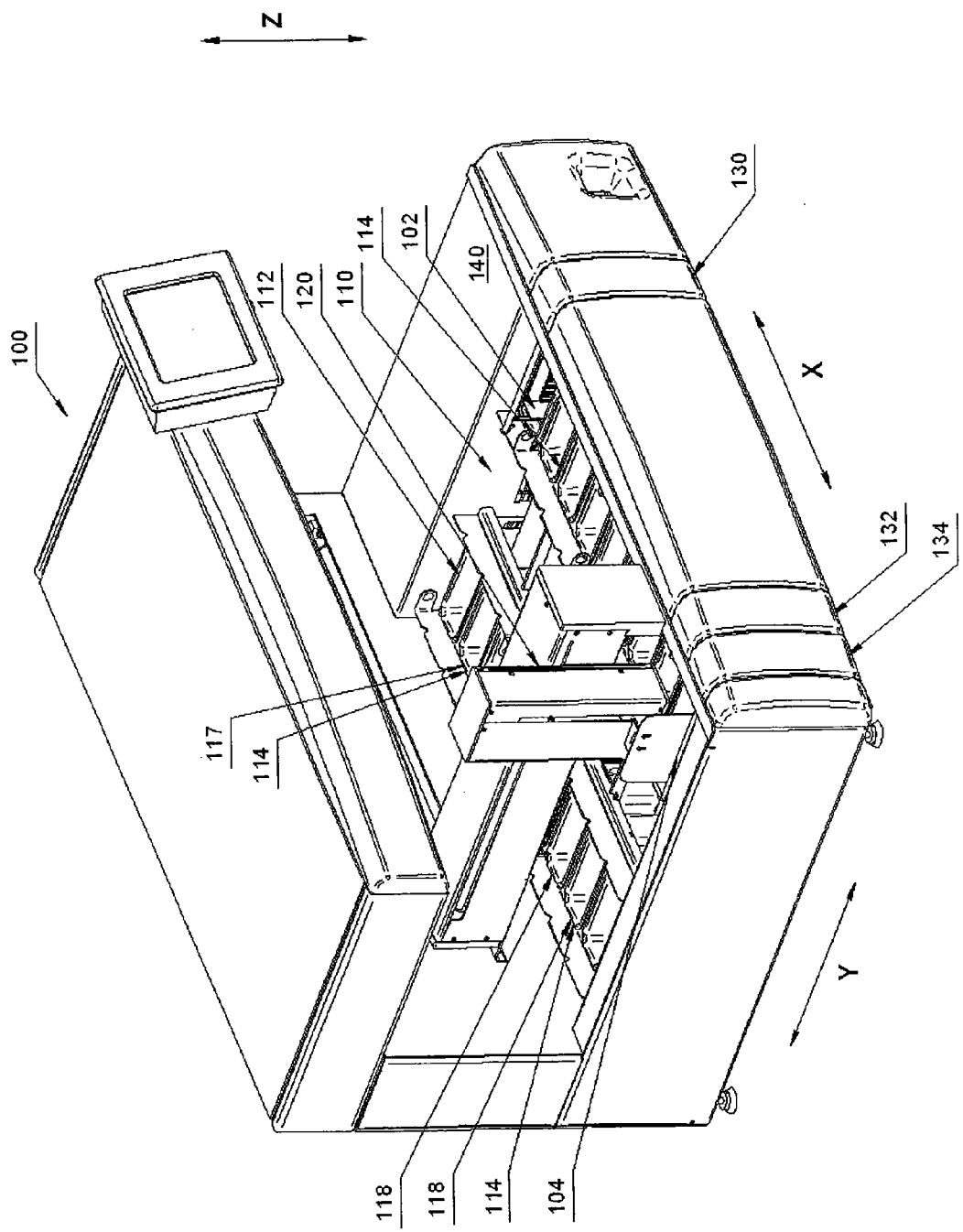
FIG. 5 is a perspective view of the slide stainer of FIG. 1, with the lifting device lowering the set of slides into a removal drawer.

As an example of non-sequential processing, first set 104 of specimen slides 102 may be picked up from loading drawer 130 to be placed into first heating station 110, as shown in FIGS. 2 and 3. Then, first set 104 of specimen slides 102 may be picked up from first heating station 110 to be placed into a processing station 114 that is not adjacent to first heating station 110, skipping over at least one processing station 114 between first heating station 110 and the processing station 114 into which first set 104 of specimen slides 102 is placed, as shown in FIG. 4. FIG. 5 shows first set 104 of specimen slides 102 having been lowered into removal drawer 134 for removal from apparatus 100. Note that, throughout the process illustrated in FIGS. 1-4, second set 106 of specimen slides 102 remains in rinse station 117.

As an example of sequential processing (not shown), second set 106 of specimen slides 102 would be placed in the same processing stations (in the same order) as the first set 104 of specimens slides 102.

Figure 6:
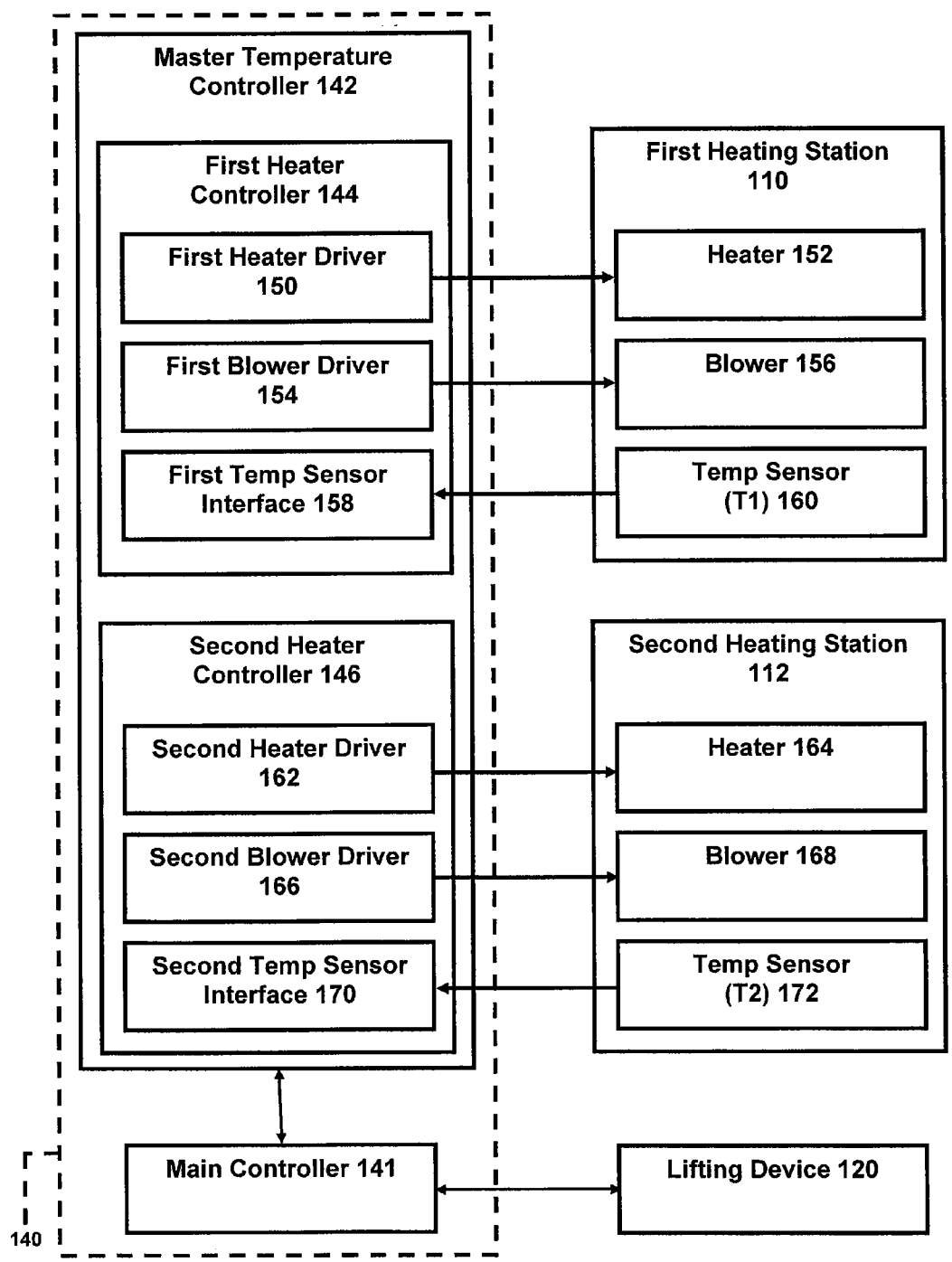
FIG. 6 is an exemplary embodiment of a simplified electrical schematic drawing showing control of first and second heater stations and the lifting device.

In an exemplary embodiment, shown schematically in FIG. 6, controller 140 includes a main controller 141 and a master temperature controller 142. Master temperature controller 142 may regulate temperature of first heating station 110 and second heating station 112 under direction from main controller 141. In the illustrated embodiment, master temperature controller 142 includes a first heater controller 144 for regulating a first temperature T1 at first heating station 110 and a second heater controller 146 for regulating a second temperature T2 at second heating station 112. Regulation of second temperature T2 may be performed independently of regulation of first temperature T1. In an alternative embodiment, master temperature controller 142 may include a single temperature controller that performs the functions of first and second heater controllers 144, 146 (represented by dashed lines between controllers 144, 146 in FIG. 6).

First heater controller 144 includes a first heater driver 150 for driving a heater 152 at first heating station 110, a first blower driver 154 for driving a blower 156 at first heating station 110, and a first temperature sensor interface 158 for receiving temperature information transmitted by a temperature sensor 160 to regulate first temperature T1 at first heating station 110.

Second heater controller 146 includes a second heater driver 162 for driving a heater 164 at second heating station 112, a second blower driver 166 for driving a blower 168 at second heating station 112, and a second temperature sensor interface 170 for receiving temperature information transmitted by a temperature sensor 172 to regulate second temperature T2 at second heating station 112.

Controller 140 may be programmed to selectively control first temperature T1, second temperature T2, a first period of time in which specimen slides 102 remain in first heating station 110, and a second period of time in which specimen slides 102 remain in second heating station 112.

In use, heating stations 110, 112 may be used to heat specimen slides 102 to remove a coating, such as paraffin wax (not shown), from the surface of specimen slides 102. Heating stations 110, 112 may also be used to dry specimen slides 102 after processing in processing stations 114. Therefore, it is possible that specimen slides 102 may be inserted into heating stations 110, 112 more than one time during processing in apparatus 100.

Figure 7:
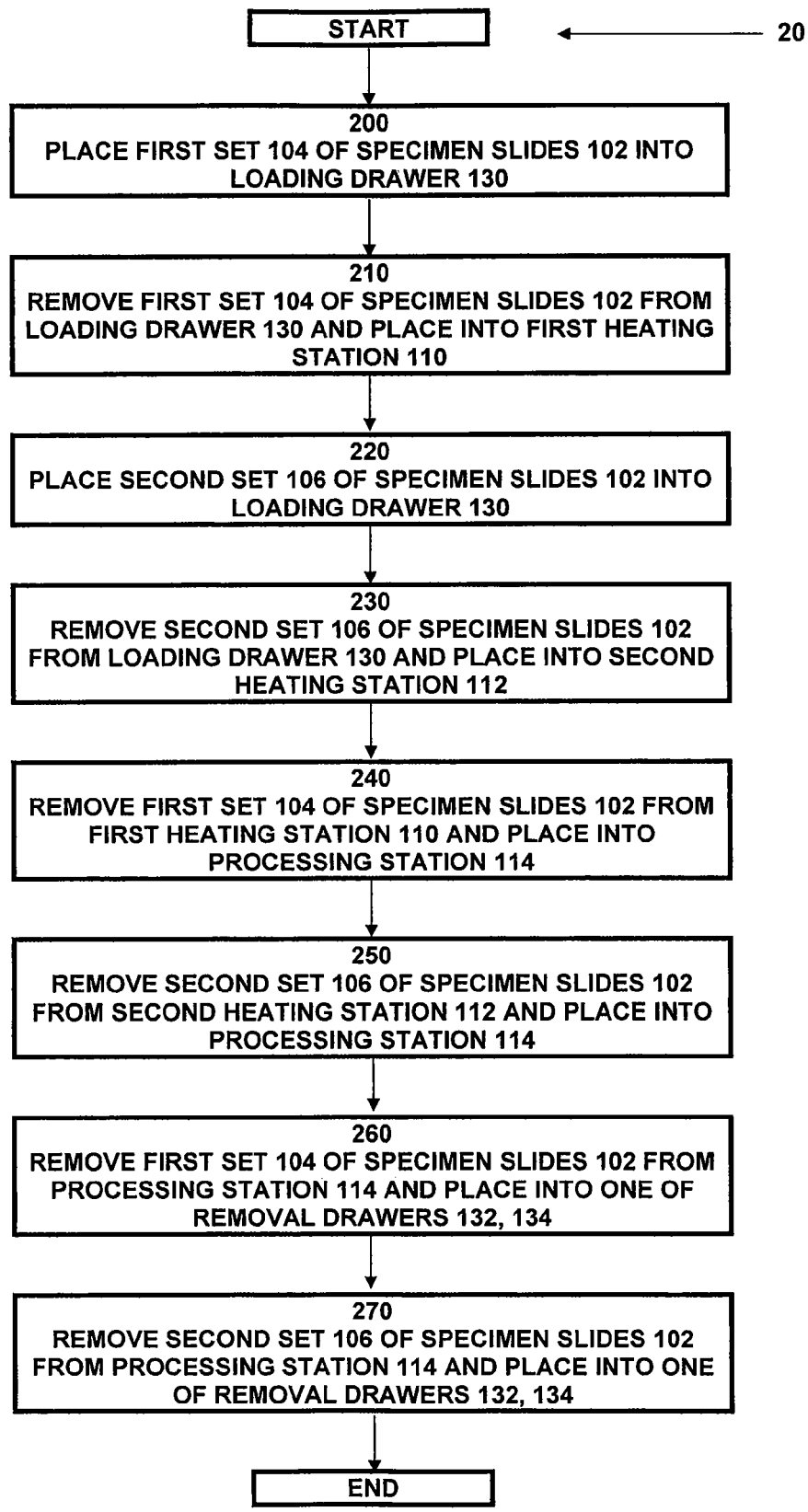
FIG. 7 is a flow chart showing operation of the slide stainer according to an exemplary embodiment of the present invention.

FIG. 7 depicts a flow chart 20 of exemplary steps for treating hematological, cytological, or histological slides in accordance with an exemplary embodiment of the present invention. The steps will be described with references to FIGS. 1-6. In step 200, first set 104 of specimen slides 102 are placed into loading drawer 130 and then, in step 210, removed from loading drawer 130 by lifting device 120 and placed into first heating station 110. First heating station 110 may be set to first temperature T1.

In step 220, second set 106 of specimen slides 102 are placed into loading drawer 130 and then, in step 230, removed from loading drawer 130 by lifting device 120 and placed into second heating station 112. Second heating station 112 may be set to second temperature T2.

Second set 106 of specimen slides 102 may be inserted into second heating station 112 while first set 104 of specimen slides 102 is in first heating station 110 or second set 106 of specimen slides may be inserted into second heating station 112 after first set 104 of specimen slides 102 may have already been removed from first heating station 110.

While both first and second sets 104, 106 of specimen slides 102 are in their respective heating stations 110, 112, first and second sets 104, 106 of specimen slides 102 may be heated simultaneously. First temperature T1 may be set independently from second temperature T2, or, alternatively, first temperature T1 and second temperature T2 may be set together so that one control setting controls the temperature in both heating stations 110, 112. While in each respective heating station 110, 112, a coating covering each specimen slide 102, if present, may be removed by the respective heating station 110, 112.

In steps 240 and 250, respectively, each of first and second sets 104, 106 of specimen slides 102 is serially removed from its respective heating station 110, 112 by lifting device 120 and placed in at least one of a plurality of processing stations 114 in a predetermined non-sequential order. While FIG. 7 shows first set 104 of specimen slides 102 being place into a processing station 114 prior to second set 106 of specimen slides, those skilled in the art will recognize that second set 106 of specimen slides 102 may be placed into processing station 114 prior to first set 104 of specimen slides 102, in which case steps 240 and 250 are reversed. In steps 260 and 270, respectively, each of first set 104 and second set 106 of specimen slides 102 are removed from processing station 114 and placed into one of removal drawers 132, 134 for removal from apparatus 100.

At a predetermined time after first set 104 of specimen slides 102 is removed from first heating station 110, a third set 108 of specimen slides 102 placed in loading drawer 130 (shown in FIG. 5), may be picked up from loading drawer 130 by lifting device 120 and placed into first heating station 110.

In an alternative embodiment of the present invention, first heating station 110 may be set to first temperature T1, and second heating station 112 may be set to second temperature T2, higher than T1. First set 104 of specimen slides 102 may be placed into first heating station 110 and heated to first temperature T1. First set 104 of specimen slides 102 may then be removed from first heating station 110, placed into second heating station 112 and heated to second temperature T2.

Movement of first and second sets 104, 106 of specimen slides 102 among loading drawer 130, heating stations 110, 112, processing stations 114, and removal drawers 132, 134 is performed by moving first and second sets 104, 106 of specimen slides 102 along three orthogonal axes X, Y, Z, shown in FIGS. 1-5. The aforementioned operations may be programmed into controller 140 and, with the exception of loading first and second sets 104, 106 of specimen slides 102 into loading drawer 130 and removing first and second sets 104, 106 of specimen slides 102 from removal drawers 132, 134, carried out independently from outside intervention.

In another exemplary method of use, first set 104 of specimen slides 102 may be inserted into first heating station 110, which is set to first temperature T1. First temperature T1 is sufficient to remove the coating, if present, from first set 104 of specimen slides 102. First set 104 of specimen slides 102 is then removed from first heating station 110 and inserted into at least one of processing stations 114 where first set 102 of specimen slides 104 is processed. First set 104 of specimen slides 102 may be inserted into the at least one of processing stations 114 in a non-sequential order. Prior to inserting first set 104 of specimen slides 102 into one of removal drawers 132, 134, first set 104 of specimen slides 102 is inserted into second heating station 112, which is set to second temperature T2, different from T1, where first set 102 of specimen slides 104 is dried.

After first set 104 of specimen slides 102 is removed from first heating station 110, third set 108 of specimen slides 102, shown in FIG. 5, may be moved from loading drawer 130 and inserted into first heating station 110. While first set 104 of specimen slides 102 is being processed in one of processing stations 114, third set 108 of specimen slides 102 may heated in first heating station 110.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A method of treating hematological, cytological, or histological slides comprising:
    a) placing a first set of specimen slides into a first heating station, the first set of specimen slides comprising a wax coating, the first heating station comprising a first source of hot air;
    b) blowing the hot air from the first source on the first set of specimen slides in the first heating station, thereby heating the first set of specimen slides to a first temperature to melt the wax coating off of the first set of specimen slides;
    c) placing a second set of specimen slides into a second heating station, the second set of specimen slides comprising a wax coating, the second heating station comprising a second source of hot air;
    d) blowing the hot air from the second source on the second set of specimen slides in the second heating station, thereby heating the second set of specimen slides to a second temperature independent from the first temperature to melt the wax coating off of the second set of specimen slides;
    e) removing each of the first and second sets of specimen slides from its respective heating station;
    f) placing each of the first and second sets of specimen slides into a plurality of processing stations in a predetermined non-sequential order;
    g) placing the first set of specimen slides into the first heating station after processing the first set of specimen slides;
    h) blowing the hot air from the first source on the first set of specimen slides in the first heating station to dry a reagent from the processing off of the first set of specimen slides;
    i) placing the second set of specimen slides into the second heating station after processing the second set of specimen slides;
    j) blowing the hot air from the second source on the second set of specimen slides in the second heating station to dry a reagent from the processing off of the second set of specimen slides.

2. The method according to claim 1, wherein step (f) comprises moving the first and second sets of specimen slides along three orthogonal axes to the plurality of processing stations.

3. The method according to claim 1, wherein each of the first and second sets comprises a coating and wherein the method further comprises the step of heating the first and second sets of specimen slides to remove the coating from the first and second sets.

4. The method according to claim 1, wherein step (f) is performed prior to either of steps (a) or (c).

5. The method according to claim 1, wherein the first set of specimen slides is in the first heating station and the second set of heating slides is in the second heating station and wherein step (e) comprises removing the first set after a first period of time and removing the second set after a second period of time, wherein the first and second times are different.

6. The method according to claim 5, further comprising varying the first period of time and the second period of time.

7. The method according to claim 5, further comprising selectively controlling the first temperature, the second temperature, the first period of time, and the second period of time.

8. The method according to claim 1, further comprising selecting one of the first heating station, the second heating station, and one of the plurality of processing stations into which the first and second sets are to be placed; selecting the temperature of the first heating station and the temperature of the second heating station; and determining a duration of time that each of the first and second sets are in the respective first and second heating stations and the plurality of processing stations.

9. The method according to claim 1, wherein the step of placing the second set of specimen slides into the second heating station is performed while the first set of specimen slides is in the first heating station.

10. The method according to claim 1, further comprising:
placing the second set of specimen slides into the second heating station after the first set of specimen slides is placed into the first heating station; and
removing the second set of specimen slides from the second heating station before removing the first set of specimen slides from the first heating station.

11. The method according to claim 1, further comprising removing the first set of specimen slides from the first heating station and placing a third set of specimen slides into the first heating station while the second set of specimen slides is still in the second heating station.

12. The method according to claim 1, wherein the second temperature is different from the first temperature.

13. The method according to claim 1, further comprising using a first controller to heat the first set of specimen slides to the first temperature and using a second controller to heat the second set of specimen slides to the second temperature.

14. The method according to claim 1, further comprising the step of placing the first set of specimen slides into the second heating station and heating the first set of specimen slides to the second temperature.

15. The method according to claim 14, further comprising, after removing the first set of specimen slides from the first heating station, placing a third set of specimen slides into the first heating station.

16. The method according to claim 1, further comprising heating the first and second sets of specimen slides simultaneously.

17. A method of processing a plurality of specimen slides comprising:
a) placing a set of specimen slides into a heating station, the set of specimen slides comprising a wax coating, the heating station comprising a source of hot air;
b) blowing the hot air from the first source on the set of specimen slides, thereby heating the set of specimen slides to a temperature with the heating station to melt the wax coating off of the set of specimen slides;
c) removing the set of specimen slides from the heating station and placing the set of specimen slides into a slide processing station;
d) placing the set of specimen slides into the heating station after processing the set of specimen slides; and
e) blowing the hot air from the source on the set of specimen slides in the heating station to dry a reagent from the processing off of the set of specimen slides.

18. The method according to claim 17, wherein step (c) comprises moving the set of specimen slides along three orthogonal axes.

* * * * *